United States Patent [19]

Kossovsky

[11] Patent Number: 5,798,220
[45] Date of Patent: Aug. 25, 1998

[54] ASSAY FOR HUMORAL IMMUNITY TO MACROMOLECULES

[75] Inventor: Nir Kossovsky, Los Angeles, Calif.

[73] Assignee: The Regents of the University of California, Oakland, Calif.

[21] Appl. No.: 450,860

[22] Filed: May 25, 1995

Related U.S. Application Data

[63] Continuation of Ser. No. 29,775, Mar. 11, 1993, abandoned.

[51] Int. Cl.⁶ ................................................. G01N 33/53
[52] U.S. Cl. .............................. 435/13; 435/7.1; 435/7.92; 435/7.95; 436/524; 436/525; 436/527; 436/528; 436/531; 436/72
[58] Field of Search .................. 422/57, 58; 436/506, 436/519, 522, 524, 528, 529, 530, 72, 73, 809, 810, 525, 531, 527; 435/7.1, 7.92, 7.95, 13, 291, 299

[56] References Cited

U.S. PATENT DOCUMENTS

| | | |
|---|---|---|
| 3,966,580 | 6/1976 | Janata et al. . |
| 4,299,916 | 11/1981 | Litman et al. . |
| 4,780,401 | 10/1988 | Heusser et al. . |
| 4,973,493 | 11/1990 | Guire . |
| 5,063,081 | 11/1991 | Cozzette et al. . |
| 5,081,048 | 1/1992 | Okahata et al. . |

OTHER PUBLICATIONS

Ronagnoli et al., "Gold–Specific T–Cells in Rheumatoid Arthritis Patients Treated with Gold", Journal of Clinical Investigation, vol. 89, Jan. 1992, pp. 254–258.

Goldblum et al, Aug. 1992. Antibodies to silicone elastomers and reactions to ventriculoperitoneal shunts, Lancet 340:510–13.

Goding, 1983, *Monoclonal Antibodies : Principles and Practice*, Academic Press, Inc., London. pp. 75–80.

Kossovsky, N. and Papasian, N.: "Clinical Reviews: Mammary Implants," Jour.Appl.Biomaterials, vol. 3 (1992) pp. 1–4.

*Primary Examiner*—Patricia Duffy
*Attorney, Agent, or Firm*—Oppenheimer Wolff & Donnelly LLP

[57] ABSTRACT

A method for detecting immunogenic responses to native macromolecules. The native macromolecule is bound to a biomaterial or pharmacologic support surface and used in an immunoassay to screen biological fluids for antibodies to the macromolecule in its bound state. The method is used to screen for immune responses to implanted biomaterials and pharmacologically administered agents where native macromolecules which have interacted with the implant are conformationally altered and elicit an immune response.

5 Claims, No Drawings

ASSAY FOR HUMORAL IMMUNITY TO MACROMOLECULES

This is a continuation of application Ser. No. 08/029,775 filed on Mar. 11, 1993 which is now abandoned.

BACKGROUND OF THE INVENTION

1. Field of the Invention

The present invention relates to methods for detecting humoral immunity to macromolecules. More particularly, the present invention involves a method for determining immunogenic responses to native macromolecules or pharmacologically administered macromolecules which are present in the body in either a conformationally altered or unaltered form.

2. Description of Related Art

A wide variety of materials are presently being introduced into patients as implants or as part of medical treatment. These biomaterials or biological implants include a wide range of materials such as polymers, metals and alloys, and ceramics. A recurring problem with the introduction of these biomaterials into the body is possible adverse reactions and eventual rejection of the implant or other complication.

It is widely recognized that the mammalian body's adverse reaction to implanted biomaterials is based at least in part on an immunogenic response. The introduction of the biomaterial into the biological milieu of the body is followed by the adsorption of native macromolecules or proteins to the synthetic surface. Over time, the adsorbed native proteins undergo biophysical and biochemical interactions with the synthetic surface. These interactions are thought to eventually result in conformational changes in the native macromolecules. Since denatured macromolecules and complexes of macromolecules and synthetic biomaterials are potentially immunogenic, their role in immunological reactions to synthetic biomaterials has been recently implicated. Silicone breast prosthesis have come under close scrutiny due to concerns over possible adverse biological activity of the implanted device. The implant site of a silicone breast prosthesis is characterized grossly by a fibrous capsule and histologically by a variable mixture of dense collagen, fibroblasts, macrophages, giant cells, lymphocytes and sometimes plasma cells. This chronic inflammatory process has been often described as a "non-specific" foreign body reaction. The clinical consequences of the inflammation are not well understood.

Currently, the concern expressed by the scientific community over the biological activity of silicones is fueled by three factors: (a) the apparent absence of scientific data on the long-term human experience with silicone implants; (b) anecdotal human case studies suggesting silicone-associated immunological phenomena, and (c) animal experimental data suggesting that silicones have both adjuvant and immunogenic activities. Most recently, Goldblum and others demonstrated for the first time increased levels of silicone specific antibodies in humans. (Goldblum R. m., Pelley R. P., O'Donell A. A., Pyron D.; Heggers J. P.: Antibodies to silicone elastomers and reactions to ventriculoperitoneal shunts. Lancet 1992; 340:510–513).

The polydimethylsiloxane type silicones used in medical implants are highly hydrophobic materials with relatively low surface energies of approximately 24 J/cm. They may therefore create significant environmental disturbances in the normally hydrophilic extracellular space. Their relatively small sphere of influence is defined by their Debye radius, which is proportional to their surface energy. As hydrophobic residues which would normally remain hidden in the native environment of biological moieties come within this debye radius, they are attracted to the silicone implant surface and undergo hydrophobic interactions. As a result, varying degrees of conformational change and corresponding denaturations of the protein is believed to occur. (Falb R. D., Grode G. A., Takahashi M. T. and Leininger R. I.: NIH Contract PH-43-64-496, Development of Blood Compatible Polymeric Materials, Report of 30 Mar. 1967; Chattoraj D. K. and Bull H.: Electrophoresis of adsorbed proteins. J Am Chem Soc 1959; 81:5128–5133; and Kochwa S., Brownell M., Rosenfield R. E. and Wasserman L. R.: Adsorption of proteins by polystyrene particles. I. Molecular unfolding and acquired immunogenicity of IgG. J Immunol 1967; 99:981–986).

In order to further investigate the role of conformationally altered macromolecules in the above observed immune responses, it would be desirable to develop a method which is capable of measuring immunogenic responses to native macromolecules and pharmacologically administered macromolecules which have been conformationally altered and/or denatured by interaction with implanted biomaterials. In addition, it would be desirable to provide a method which is also capable of measuring immune responses to unaltered native macromolecules. Such a method would be useful in studying and detecting autoimmune diseases where immune responses are observed in the absence of implanted foreign biomaterials.

SUMMARY OF THE INVENTION

The present invention provides methods and compositions which are capable of detecting and measuring immunogenic responses to native and pharmacologically administered macromolecules present in a mammal. The invention is applicable to detecting immunogenic responses to both conformationally altered and unaltered native macromolecules.

The present invention is based on a method where a test surface is coated with a macromolecule support material to provide a macromolecule support surface. The support material is selected to correspond to the particular implant biomaterial being investigated. For example, the test surface is coated with silicone to form a silicone support surface if the immunogenic response to macromolecules altered by interaction with silicone is being investigated. The macromolecule support surface is next treated with a selected native macromolecule to attach the native macromolecule to the support material. The bound native macromolecule interacts with the support material and may become conformationally altered depending upon the particular support material chosen. For example, the native macromolecule will become substantially denatured when the support surface is silicone. On the other hand, the native macromolecule will be substantially unaltered conformationally when the support surface is a benign material such as cellobiose.

The bound native macromolecule is then used to screen biological fluids for specific immunoglobulin which may have been generated as part of an immunogenic response to the native macromolecule in its conformational state when bound to the support material in vivo. Any of these specific immunoglobulin present in the fluid will bind to the bound native macromolecules to form a macromolecule/immunoglobulin complex which can be detected by any of the well-known immunoassay detection techniques.

The present invention provides a simple, quick and accurate method for screening biological fluids to detect the presence of antibodies or immunoglobulins which are generated as part of an immune response to a wide variety of native macromolecules which have been conformationally altered by interaction with various implanted biomaterials. The method is extremely versatile since the support material coating on the test surface can be chosen from the whole spectrum of polymers, metals and ceramics which are presently used as implanted biomaterials. When this feature is taken in combination with the multitude of native macromolecules which can be tested for, the method provides a powerful procedure for screening possible adverse immunogenic reactions in a majority of the situations where biomaterials are implanted into a patient.

As another feature of the present invention, the support material which is coated onto the test surface can be a biologically benign material which does not alter the conformation of the native macromolecule. The unaltered bound macromolecules can then be used to screen for the presence of autoantibodies which may be generated against unaltered native macromolecules in certain autoimmune diseases.

The above described and many other features and attendant advantages of the present invention will become better understood by reference to the following detailed description.

DETAILED DESCRIPTION OF THE INVENTION

The present invention has wide application to the detection of immunoglobulin which are produced as part of an immune response to macromolecules present in the mammalian body. These macromolecules which naturally occur in the body are commonly referred to as "native" macromolecules or proteins. The invention may be used to detect immunoglobulin which are produced in response to native macromolecules which are conformationally altered due to interaction with synthetic biomaterials or native macromolecules which have slight alterations in their conformations or are unaltered.

Examples of native macromolecules include plasma proteins, matrix proteins or cell membrane phospholipids. Specific examples include fibrinogen, collagen, fibronectin, laminin, sphingomyelin, phosphatidylcholine, myelin, and estrogen.

When various synthetic biomaterials are introduced into the body, one or more native macromolecules may be adsorbed or otherwise interact with the biomaterial. This interaction may result in the alteration of the conformation of the macromolecule. The degree to which the macromolecule conformation is altered depends upon the particular biomaterial. Biomaterials presently being introduced into mammalian bodies include metals, polymers, glasses and ceramics. For some of these biomaterials, the degree to which absorbed native macromolecules are conformationally altered is slight. However, most biomaterials interact with the macromolecules to alter their conformations to some degree with denaturization occurring in many cases. The more hydrophobic a biomaterial is, the more it is expected to alter the conformation of the macromolecule which interacts with it.

Examples of biomaterials include silicone, dimethylpolysiloxane, stainless steel, polytetrafluoroethylene, alumina, zirconia, polyurethane, and calcium phosphate ceramics. The biomaterials may be introduced into the body in a variety of different forms. The biomaterial may be in the form of an implant device or other solid material. The biomaterial may also be in the form of a fluid.

The method of the present invention is designed to detect the presence of immunoglobulin which are produced in vivo as part of an immunogenic response to the native macromolecules which are absorbed onto or otherwise interact with the implanted biomaterial. The method is similar to and follows the same basic procedures which are used in conventional immunoassays. The principle differences are: 1) the test surface is first coated with a biomaterial or macromolecular support surface; and 2) the immunogenic molecule which is adsorbed onto the macromolecule support surface is the native macromolecule. The bound native macromolecule may be conformationally altered depending upon the particular biomaterial macromolecular support surface being used. The bound native macromolecule functions in the same manner as a bound antigen which is used to screen for antibodies in various biological fluids according to the well-known ELISA procedures or other immunoassay techniques which utilize a surface bound antigen to screen for antibodies reactive with the antigen.

The test surface can be any of the anchoring surfaces commonly used in immunoassays. Plastic plates with test wells (ELISA plates) are a preferred test surface. However, polymer beads and other particulate support materials may be used. Examples of suitable test surfaces include polyvinyl chloride, polystyrene, and polycarbonate. A basic requirement for the immunoassay test surface is that it be suitable for receiving a coating of the desired biomaterial or macromolecule support material.

The biomaterial or macromolecule support materials are classified according to their surface characteristics and their ability to cause conformational alterations and possible denaturization of the native macromolecules which become bound to or otherwise interact with the support material. Support materials, such as silicone and polyethylene are hydrophobic and tend to have surface energies which cause significant alterations in the conformation of native macromolecules which bind to these materials. On the other hand, many basic sugars have low surface energies so that native macromolecules bound to these support materials remain substantially unaltered. Exemplary low surface energy or non-denaturing support materials include cellobiose, trehalose, isomaltose, maltose, nystose, maltotriose and nitrocellulose.

The particular material which is coated onto the test plate to form the macromolecule support surface is chosen depending upon the immunogenic response which is being investigated. For example, to test for immune responses to silicone implants, the test surface is coated with silicone. For metal implants, the test surface is coated with the particular metal. For autoimmune investigations where antibodies to unaltered native macromolecules are being detected, one of the above listed non-denaturing support materials are used. On the other hand, if the administered agent is a pharmacologic agent and the native macromolecule is one of the components of red blood cells or other native cellular structures, the deposition sequence may be reversed and a film of membrane phospholipids may be deposited first on the supporting materials such as polycarbonate or polystyrene. Subsequent to the deposition of the membrane phospholipid, a pharmacologic agent is then allowed to adsorb to the phospholipid support. Exemplary pharmacological agents include insulin, penicillin, quinidine, methyldopa, hydralazine, and procainamide. A pharmacological agent can be any macromolecule which is administered to the mammalian body.

The coatings may be applied by any of the common deposition procedures. Suitable procedures include vapor phase deposition, solution precipitation, solution evaporation and adsorption from bulk phase. The coating is applied so that it provides a suitable anchoring surface for the native macromolecules. The coating thicknesses and other characteristics are chosen so that the coating does not interfere with the immunoassay. For example, when colorometric detection methods are being used, the macromolecule support material should be transparent to prevent interference with absorbance measurements. A few exemplary combinations of test surfaces and macromolecule support surfaces are as follows: polystyrene/silicone; polyvinyl-chloride/silicone; polystyrene/phospholipid and polystyrene/gold.

In certain situations, the test surface and the macromolecule support surface may be the same material so that a separate support coating will not be required.

Prior to the actual assay, the test surface coated with the selected support material must be treated with the native macromolecule or exogenously administered macromolecule which is suspected of eliciting an immune response. The treatment protocol simply involves contacting the macromolecule with the coated test surface for a sufficient time to allow adsorption onto the coated test surface. This typically involves adding a solution containing the macromolecule to a coated test well in an ELISA plate or mixing the macromolecule solution with coated support particles. The step of adsorbing the native macromolecules onto the macromolecule support surface can be accomplished by using any of the well-known procedures for adsorbing antigens onto a support or anchor surface.

Exemplary combinations of macromolecule support systems with macromolecules are as follows: silicone/fibrinogen; dimethylpolysiloxane/fibrinogen; stainless steel/collagen; phospholipids/penicillin; dimethylpolysiloxane/fibronectin; dimethyl-polysiloxane/insulin; phospholipids/hydralazine; polytetrafluoroethylene/fibrinogen.

The next step in accordance with the method of the present invention involves using the bound native macromolecule to screen biological fluids for the presence of immunoglobulin reactive with the bound macromolecule. This step is conducted in the same manner as conventional immunoassays. Typically, the fluid being tested, usually serum, is simply added to the test well containing the bound native macromolecule. Biological fluids other than serum which are commonly tested for immunoglobulin may also be tested using the present invention. The specific test parameters, such as temperature and reaction times, may be varied depending upon the particular assay as is well known in the art. In accordance with conventional practice, the test surface is washed after a given time to remove unbound immunoglobulin.

The immunoglobulin which remain attached to the bound native macromolecules after washing are detected by conventional immunoassay techniques. These techniques include spectrophotometry, immunofluorescence, immmunochemiluminescence, and radioimmunoassay.

Examples of practice are as follows:

EXAMPLE 1

This example demonstrates the use of the method of the present invention to test the serum of human patients with silicone breast implants to determine if antibodies to silicone altered native macromolecules are present.

Three groups of sera were assayed: a reference group of 47 non-implanted age matched healthy women, a group of 249 women implanted with silicone breast prostheses, and a group of 39 non-implanted women with various known rheumatologic diseases. Antigenic targets for testing serum IgG affinity to various silicone altered native macromolecules were created by coating standard 96-well polystyrene ELISA plates with silicone fluid; to these silicone-treated wells, macromolecules that were thought to adsorb to the silicone surfaces in the tissues were added in solution. These macromolecules included plasma proteins such as fibrinogen and those found in serum free of IgG; matrix proteins such as collagens, fibronectin and laminin; and cell membrane phospholipids such as sphingomyelin and phosphatidylcholine.

Specifically, standard 96 well polystyrene ELISA plates (Fisher) were treated with 300 ul per well dimethylpolysiloxane (Dow Corning 200 Fluid) oil for 5minutes. The plates were emptied gravitometrically, covered, and centrifuged upside down at 1000 rpm for 10 minutes. The plates were then placed upside down in a sterile hood for 2 hours. The coated wells were then treated with 275 ul of one of six solutions: (1) normal phosphate buffered saline (PBS), pH 7.4 control; (2) fibrinogen (8 ug/ml) in PBS, pH 7.4; (3) serum free of IgG (8 ug/ml) in PBS, pH 7.4; (4) a solution containing 4 ug each of fibronectin and laminin per ml of PBS pH of PBS pH 7.4; (5) a 1:10 dilution in PBS, pH 12.5 of a solution containing 24 ug each of collagens VI, VIII and X per ml of 0.5M acetic acid, pH 0.91; and (6) a 1:10 dilution in PBS, pH 7.4 of a solution containing 36 ug each of sphingomyelin and phosphatidylcholine per ml of methanol (Sigma Chemicals). The plates were covered and incubated at 4° C. for 7 days.

After incubation the above plates were emptied of the solutions gravitometrically. 150 ul of a 1:100 dilution of patient serum in 50 mM tris buffered saline (pH 7.5) were then added to each well. The plates were incubated at 37° C. for two hours. Potential IgG binding was measured in triplicate following standard ELISA protocol with alkaline phosphatase conjugated to goat anti-Human IgG (Zymed) as the secondary antibody and p-nitrophenylphosphate (PNPP) serving as the substrate.

Absorbance was measured at 405 nm. Non-specific IgG binding was controlled for by subtracting absorbance values for serum IgG bound to untreated polystyrene wells. This also controlled for variations in absolute serum IgG levels.

Chi-square goodness of fit procedures showed that all three groups' frequency distribution of IgG binding affinity to the various surfaces (after outliers of 3 sigma were excluded) followed a Gaussian distribution. The frequency distributions of the reference and implanted populations were compared and found to be superimposable within three standard deviations; mean values were compared for pairs of the three populations by using t tests, and variances were compared using Bartlett's procedure (ratio of variances). A p value of 0.10 was used to assess significance since a type II error, or false negative, is the more serious mistake in this context. The means of the truncated implant and reference populations showed no statistically significant differences; their variances were also comparable, with the exception of the fibrinogen-silicone curve. Outliers of these superimposable curves were therefore considered significant. A conservative threshold was set at four standard deviations above the mean of the reference population (encompassing a theoretical 99.996% of the group); a positive reaction was defined as binding affinity greater than this threshold.

Allowing for overlaps, the following percentages of 249 implanted women had IgG that reacted positively to the respective macromolecules: 3.6% to fibronectin-laminin adsorbed to silicone, 1.6% to silicone film alone, 1.2% to phospholipids adsorbed to silicone, and 0.4% to fibrinogen adsorbed to silicone. None of the sera from the reference population or the rheumatologic population were positive. This example shows that the method of the present invention is an effective procedure for detecting immunogenic response to native macromolecules.

EXAMPLE 2

In this example, the method of the present invention was used to detect humoral responses to fibronectin and laminin physically adsorbed to biomaterials other than silicone. The biomaterials included polystyrene, acid washed polystyrene and cellobiose coated onto polystyrene. As mentioned above, cellobiose creates a glassy state that tends to preserve the native aqueous conformation of biological molecules even when the latter are adsorbed onto solid phase surfaces.

The polystyrene ELISA plates were prepared as described in Example 1. Rather than coating with silicone as a first step, one of four different surface treatments was executed: 1) plates were used as received ("untreated"); 2) wells were treated with 300 ul of 6N HCl for one hour ("acid washed"); 3) and 4) plates were acid washed, treated with 300 ul of 100 mM cellobiose in HPLC grade water, and after overnight incubation at 4° C., centrifuged upside down at 1000 rpm for 10 minutes. Sets 1) and 2) were subsequently treated with 275 ul of a solution containing 4 ug each of fibronectin and laminin per ml of 100 mM sodium bicarbonate buffer, pH 9.6, and the plates were incubated at 4° C. for 7 days; set 3) was treated with 275 ul of a solution containing 4 ug each of fibronectin and laminin per ml of 20 mM sodium phosphate buffer, pH 7.5 ("low ionic buffer/cellobiose"); and set 4) was treated with 275 ul of a solution containing 4 ug each of fibronectin and laminin per ml of 100 mM sodium bicarbonate buffer, pH 9.6 ("high ionic buffer/cellobiose"). Both sets 3) and 4) were incubated overnight at 4° C. All four sets were then coated with patient sera as described in Example 1.

Again, three groups of sera were assayed: A) a group of 17 implanted patients whose IgG reactivity to fibronectin-laminin on silicone tested above two standard deviations, 8 (the supply of blood from the ninth patient had been exhausted in Example 1) of which had shown a positive reaction (reactivity above four standard deviations); B) a group of 17 random implanted patients whose test values were within two standard deviations; and C) a group of 17 random healthy control patients. A positive reaction was defined as in Example 1.

Of the 17 group A sera, only those from the subgroup of the 8 reactive patients bound avidly to fibronectin-laminin adsorbed to the four modified polystyrene surfaces. Of these 8 patients, sera from 5 reacted to both untreated and acid washed polystyrene, sera from 3 reacted to low ionic buffer/cellobiose, and sera from 2 reacted to high ionic buffer/cellobiose. The test results show that 1% of the total breast implant group exhibited IgG reactivity to fibronectin laminin on both silicone and cellobiose. None of the sera from groups B or C were positive. In terms of clinical correlation, the two patients who reacted positively to the native matrix protein molecule adsorbed to cellobiose for whom clinical data were available reported severe systemic illnesses.

In our interpretation, sera that showed significant binding to the non-denatured matrix proteins physically adsorbed to cellobiose would be more likely than other sera to react in vivo with non-denatured, native matrix proteins. The latter scenario would be consistent with the development of autoantibodies and would provide the pathophysiologic mechanism for the development of so-called silicone associated autoimmune disease.

EXAMPLE 3

Other examples include testing insulin dependent diabetics for sensitivity to insulin and/or insulin/silicone complexes. Insulin dependent diabetics inject themselves with varying doses and formulations of insulin using standard syringe injection devices. These syringes are typically lubricated with a fine layer of silicone oil (polydimethylsiloxane) and experiments have shown that insulin tends to emulsify the silicone, thereby producing small droplets of silicone coated with insulin which is one of the many products which diabetics dependent on insulin, tend to inject into themselves as part of the therapeutic program. To test whether the combination of insulin in the setting of silicone, a known adjuvant, induces immunity in these patients, appropriate immunoassay support plates are coated with a fine film of polydimethylsiloxane fluid similar to the type used to coat injection syringes. To this film, a solution of insulin is added. The insulin is allowed to adsorb to the silicone surface. The unbound silicone and insulin are then removed and excess material is washed and the plates are then filled with biological fluids containing immunoglobulins whose reactivity or affinity to the combination is being assayed.

EXAMPLE 4

As another example, some patients who have been treated with penicillin injections or received other pharmacologic agents such as hydralazine tend to develop lupus-like or other forms of other hypersensitivity. The presumed biological mechanism consists of the adsorption of the pharmacologic agent such as penicillin or hydralazine to the surface of red blood cells. To assay for immunity against the complex of drug and red blood cell, standard immunoassay support plates are coated with a film of membrane derived phospholipids. After coating the plates, drug in solution is added to the wells of the immunoassay plates that have been coated with the phospholipid and the drugs are allowed to adsorb to the phospholipid films. After an appropriate amount of time, the excess or unbound drug is removed and the wells are filled with biological fluids, containing immunoglobulins for whom reactivity or affinity to the adsorbed and denatured complex of drug is being assayed.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for detecting the presence of antibodies to conformationally altered native macromolecules in biological fluid, said method comprising the steps of:
   obtaining a sample of biological fluid from a mammal wherein a biomaterial has been implanted into said mammal, said biomaterial being selected from the group consisting of silicone, stainless steel, polytetraflouroethylene, alumina, zirconia, polyurethane and calcium-phosphate ceramics;
   providing a test surface which is coated with said biomaterial to provide a support surface consisting essentially of said biomaterial;
   wherein said support surface has been treated with a sufficient amount of a native macromolecule for a sufficient time to attach said native macromolecule to said support surface to form conformationally altered native macromolecules which are attached to said test surface, said native macromolecule being selected from the group consisting of fibrinogen, fibronectin, laminin, sphingomyelin and phosphatidylcholine;

contacting said sample of biological fluid with said conformationally altered native macromolecules for a sufficient time to allow any immunoglobulin which specifically binds with said conformationally altered native macromolecule to bind thereto to form conformationally altered macromolecule/immunoglobulin conjugates;

detecting the presence of any conformationally altered macromolecule/immunoglobulin conjugates present on said test surface.

2. A method for detecting the presence of antibodies to conformationally altered native macromolecules in biological fluid according to claim 1 wherein said silicone biomaterial is dimethylpolysiloxane.

3. A method for detecting the presence of antibodies to conformationally altered native macromolecules in biological fluid according to claim 1 wherein said native macromolecule is fibrinogen.

4. A method for detecting the presence of antibodies to conformationally altered native macromolecules in biological fluid according to claim 1 wherein said native macromolecule is a cell membrane phospholipid selected from the group consisting of sphingomyelin and phosphatidylcholine.

5. A method for detecting the presence of antibodies to conformationally altered native macromolecules in biological fluid according to claim 1 wherein said native macromolecule is fibronectin or laminin.

* * * * *